(12) United States Patent
Bourelle et al.

(10) Patent No.: US 11,413,393 B2
(45) Date of Patent: Aug. 16, 2022

(54) INJECTION DEVICE WITH ADHESIVE ASSEMBLY

(71) Applicant: ENABLE INJECTIONS, INC., Cincinnati, OH (US)

(72) Inventors: Dylan L. Bourelle, Cincinnati, OH (US); Matthew J. Huddleston, Loveland, OH (US); Joetta Renee Palmer, Mason, OH (US); David Stefanchik, Morrow, OH (US); Daniel E. Waites, Wilmington, OH (US)

(73) Assignee: Enable Injections, Inc., Cincinnati, OH (US)

( * ) Notice: Subject to any disclaimer, the term of this patent is extended or adjusted under 35 U.S.C. 154(b) by 200 days.

(21) Appl. No.: 16/755,222

(22) PCT Filed: Oct. 12, 2018

(86) PCT No.: PCT/US2018/055624
§ 371 (c)(1),
(2) Date: Apr. 10, 2020

(87) PCT Pub. No.: WO2019/075337
PCT Pub. Date: Apr. 18, 2019

(65) Prior Publication Data
US 2020/0316290 A1  Oct. 8, 2020

Related U.S. Application Data

(60) Provisional application No. 62/571,579, filed on Oct. 12, 2017.

(51) Int. Cl.
*A61M 5/142* (2006.01)
*A61M 5/20* (2006.01)
*A61M 5/31* (2006.01)

(52) U.S. Cl.
CPC .......... *A61M 5/14248* (2013.01); *A61M 5/20* (2013.01); *A61M 5/31* (2013.01);
(Continued)

(58) Field of Classification Search
CPC ...... A61M 5/14248; A61M 5/20; A61M 5/31; A61M 2005/14252; A61M 2005/208; A61M 2005/3114
See application file for complete search history.

(56) References Cited

U.S. PATENT DOCUMENTS

| 5,707,348 A | 1/1998 | Krogh |
| 6,126,637 A | 10/2000 | Kriesel et al. |

(Continued)

FOREIGN PATENT DOCUMENTS

| KR | 20150052864 A | 5/2015 |
| WO | WO2011/075103 A1 | 6/2011 |
| WO | 2014099404 A1 | 6/2014 |

OTHER PUBLICATIONS

Extended European Search Report Issued by the European Patent Office for EPO Application No. 18866183.9, dated Jun. 4, 2021 (7 pages).

(Continued)

*Primary Examiner* — James D Ponton
(74) *Attorney, Agent, or Firm* — Cook Alex Ltd.

(57) ABSTRACT

An on-body medical fluid injection device with adhesive assembly includes a housing, an injection needle, a skin-facing surface that faces the skin of a patient when on the patients body, a skin adhesive carried by at least a portion of the skin facing surface and a plurality of substantially contiguous folded film segments covering the skin adhesive.

6 Claims, 12 Drawing Sheets

(52) U.S. Cl.
CPC ............... *A61M 2005/208* (2013.01); *A61M 2005/3114* (2013.01); *A61M 2209/045* (2013.01)

(56) References Cited

U.S. PATENT DOCUMENTS

| | | | |
|---|---|---|---|
| 7,014,627 B2 | 3/2006 | Bierman | |
| 2004/0102736 A1 | 5/2004 | Bierman | |
| 2011/0282293 A1* | 11/2011 | Hordum | ............... A61M 25/02 604/180 |
| 2014/0207104 A1 | 7/2014 | Vouillamoz et al. | |
| 2015/0224285 A1 | 8/2015 | Howell et al. | |
| 2015/0297867 A1 | 10/2015 | Howell et al. | |
| 2016/0082242 A1* | 3/2016 | Burton | ............... A61M 5/14248 604/506 |
| 2020/0261643 A1* | 8/2020 | Boyaval | ............ A61M 5/14248 |

OTHER PUBLICATIONS

International Search Report and Written Opinion by the International Search Authority for International Application No. PCT/US2018/055624, dated Dec. 11, 2018 (12 pages).

Examination Report issued by Intellectual Property India corresponding to India application No. 202017015789 (dated Aug. 13, 2021) (5 pages).

First Office Action issued by the China National Intellectual Property Adminstration (CNIPA) with English translation corresponding to Chinese application No. 201880073140.8 (dated Sep. 1, 2021) (14 pages).

\* cited by examiner

INJECTION DEVICE WITH ADHESIVE ASSEMBLY

CROSS-REFERENCE TO RELATED APPLICATION

This application is the U.S. National Stage of PCT International Patent Application No. PCT/US2018/055624, filed Oct. 12, 2018, which claims the benefit of U.S. Provisional Patent Application No. 62/571,579, filed Oct. 12, 2017, the disclosure of each of which is hereby incorporated by reference in its entirety.

FIELD OF THE INVENTION

The present disclosure relates generally to an on-body medical fluid injection device assembly and to the combination of an on-body medical fluid injection device and a fluid transfer device that may be associated therewith. More specifically, this application relates to an on-body injection device with a skin adhesive configuration that exposes the skin adhesive as the injection device is removed from a support structure, such as a package or transfer device. The present disclosure also relates to an assembly of the injection device and a transfer device employed to transfer medical fluid into the injection device that automatically exposes an adhesive layer of the injection device (which secures the device to a patient during the injection) upon removal of the injection device from the fluid transfer device. The present disclosure further relates to an on-body injection device skin adhesive structure that adheres to a patient's body with enhanced conformation to different body shapes.

BACKGROUND

Injection devices that are worn by a patient temporarily or for extended periods are well known in the medical field and may be referred to as on-body injection devices. The subject matter of this application relates to assemblies to secure an on-body medical fluid injection device and/or related fluid transfer device to a patient. Although the present subject matter is applicable to a variety of medical fluid injection devices and/or related fluid transfer devices, the present description specifically, and non-exclusively, refers to the on-body medical fluid injection device described in U.S. patent application publication no. 2016/0144105, filed Jun. 17, 2014. The present application also refers to the use of such an injection device in combination with a medical fluid transfer device, as described in U.S. provisional patent application No. 62/520,335, filed Jun. 15, 2017 and in U.S. provisional application No. 62/571,419, filed on the same day herewith and entitled "Fluid Transfer Device and System." All of the above applications are hereby incorporated by reference as if fully repeated herein.

SUMMARY

In a first aspect, the disclosure provides an on-body medical fluid injection device with adhesive assembly that includes a housing of an on-body injection device configured to receive a supply of medical fluid, a an injection needle carried by the housing and movable between a retracted position within the housing and an injection position extending from the housing, wherein the housing further includes a skin facing surface that faces the skin of a patient when the on-body injection device is on the patient's body. The on-body medical fluid injection device with adhesive assembly also includes skin adhesive carried by at least a portion of the skin-facing surface for securing the housing to a patient's skin during injection, and a plurality of substantially contiguous folded film segments covering the skin adhesive, each film segment including a fold line dividing the film segment into an adhesive contact portion that is releasably adhered to the skin adhesive, and a free portion that is operable upon tensioning to progressively pull the skin adhesive contact portion away from the skin adhesive.

In a second aspect, the disclosure provides an on-body medical fluid injection device with adhesive assembly including a housing of an on-body injection device configured to receive a supply of medical fluid, an injection needle carried by the housing and movable between a retracted position within the housing and an injection position extending from the housing, wherein the housing further includes a skin facing surface that faces the skin of a patient when the on-body injection device is on the patient's body. The on-body medical fluid injection device with adhesive assembly also includes a flexible skin contact substrate having one side attached to the skin facing surface on the housing and an opposed side carries skin adhesive for adhering to the skin of a patient. A protective film is removably adhered to the skin adhesive to cover the skin adhesive until the on-body injection device is used and the flexible skin contact substrate has a peripheral edge portion that is free of attachment to the on-body injection device on the one side and carries skin adhesive on the opposed side, whereby the peripheral edge portion that is unattached to the on-body injection device allows the flexible substrate to better conform to the patient.

In a third aspect, the disclosure provides an on-body medical fluid injection device with adhesive assembly comprising a medical fluid injection device and fluid transfer device configured for holding medical fluid in cooperative relation therewith. The medical fluid injection device includes a housing configured to receive a supply of medical fluid, an injection needle carried by the housing and movable between a retracted position within the housing and an injection position extending from the housing, wherein the housing further includes a skin facing surface that faces the skin of a patient when the medical fluid injection device is on a patient's skin. The medical fluid injection device also includes skin adhesive carried by at least a portion of the skin facing surface of the housing for securing the housing to the patient's skin during injection, and a plurality of substantially contiguous folded film segments covering the skin adhesive, each folded film segment including a fold line dividing the film segment into an adhesive contact portion that is releasably adhered to the skin adhesive, and a free portion that is operable upon tensioning to progressively pull the adhesive contact portion away from the skin adhesive. The fluid transfer device includes a base having a support surface, and being configured to releasably retain the medical fluid injection device on the support surface of the base, and the transfer device is further configured to engage each free portion of each film segment, whereby upon release of the medical fluid injection device from the base and separation of the medical fluid injection device from the support surface of the base, the transfer device exerts a tensioning force on the free portion of each folded film segment to remove the film from the skin adhesive.

As above noted and explained further herein, the example injection device with adhesive assembly and example methods of using the same of this disclosure provide several advantageous features. It also is to be understood that both the foregoing general description and the following detailed description are exemplary and provided for purposes of explanation only, and are not restrictive of the claimed subject matter. Further features and objects of the present disclosure will become more fully apparent in the following description of the preferred embodiments and from the appended claims.

BRIEF DESCRIPTION OF DRAWINGS

In describing the preferred embodiments, reference is made to the accompanying drawing figures wherein like parts have like reference numerals, and wherein:

FIG. 2 is a top view of the on-body injection device with adhesive assembly of FIG. 1a.

FIG. 3 is a perspective view of the underside of the injection device assembly of FIG. 1a.

FIG. 9 is an exploded perspective view of the combination of FIG. 8a.

It should be understood that the drawings are not to scale. While some details of the example injection device with adhesive assembly, including potential alternative configurations, have not been included, such details are considered within the comprehension of those of skill in the art in light of the present disclosure. It also should be understood that the present invention is not limited to the example embodiments illustrated.

DETAILED DESCRIPTION

Figure 1A:
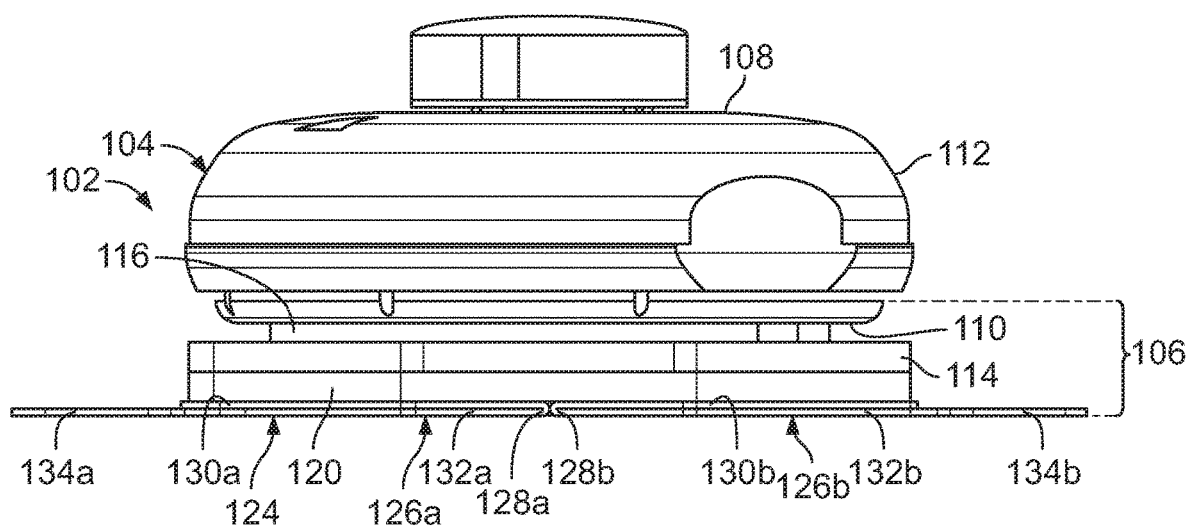
FIG. 1a is a side view of an illustrative on-body injection device with adhesive assembly having a skin adhesive configuration.
Figure 1B:
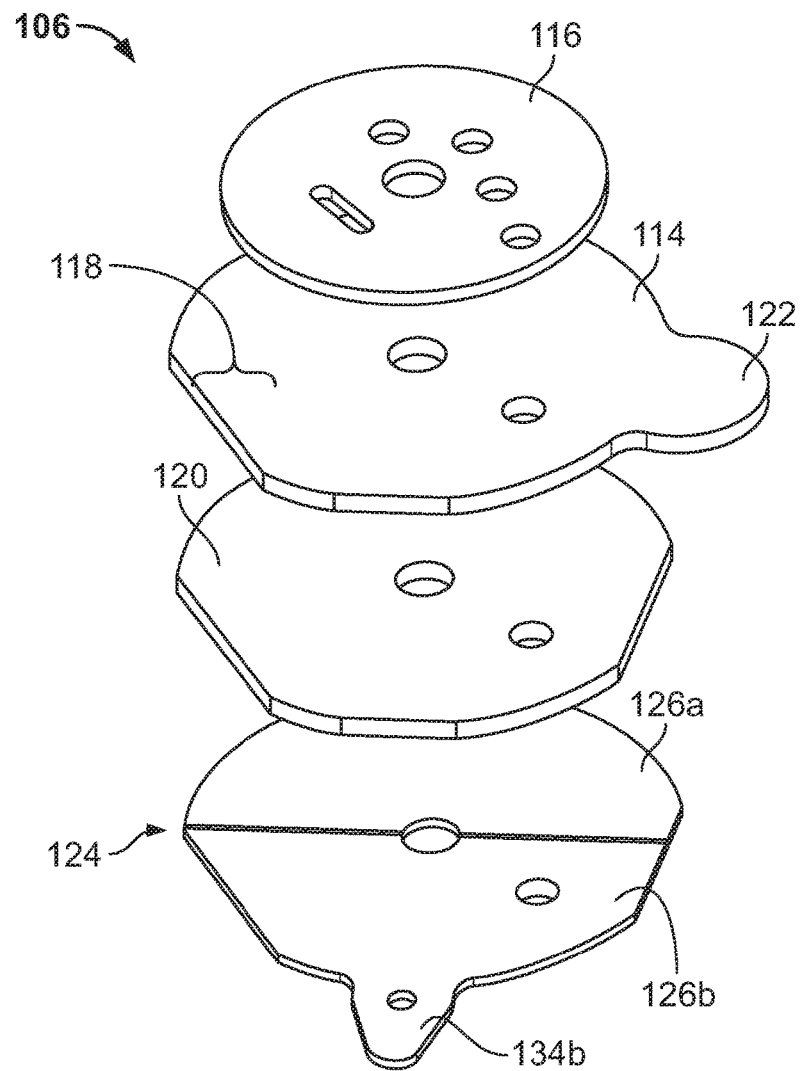
FIG. 1b is a perspective exploded view of a skin adhesive structure that is carried on the underside of the injection device assembly of FIG. 1a, with relative thicknesses exaggerated for purposes of illustration.

Turning to FIG. 1a, an example injection device with adhesive assembly is shown as an on-body medical fluid injection device with adhesive assembly 102, which includes an on-body injection device 104 and a skin adhesive structure 106 (see also FIG. 1b). The injection device 104 has an upper or top surface 108 and a bottom surface or underside 110 that faces the skin of the patient during the injection. The skin adhesive structure 106 is carried on the bottom surface 110 and functions as below described.

The details of the illustrated injection device may be found in published U.S. patent application publication no. 2016/0144105, filed Jun. 17, 2014, and herein above incorporated by reference. This device is used for purposes of illustration and not limitation. The features of the adhesive structure of the present application may also find application on other on-body injection devices of differing shape, structure or operating principle.

The illustrated on-body injection device 104 has a generally rigid plastic outer housing 112 configured to receive a supply of medical fluid and carries an injection needle movable between a retracted position within the housing 112 and an injection position extending from the housing 112. The housing 112 also includes a skin-facing surface or bottom surface 110 that faces the skin of a patient when on the patient's body. The skin-facing or bottom surface 110 is generally flat and planar, and curves convexly upwardly at its peripheral edge, as may be seen in FIG. 1a, The bottom surface 110 has a central aperture, not shown in FIG. 1a, through which the injection needle movably extends (to penetrate the patient's skin) during an injection.

As pointed out above, skin adhesive 116 is carried by at least a portion of the skin facing surface 110 for securing the housing 112 to a patient's skin during injection. The skin adhesive structure 106 is carried on the bottom surface 110 of the injection device 104. The illustrated skin adhesive structure 106 includes a skin attachment layer 114 seen in FIGS. 1a and 1b, which may be constructed of any suitable material, and preferably is flexible. In the present example, the skin attachment layer 114 is shown as a flexible non-woven polymeric material, or PET material, which may be referred to as a non-woven carrier substrate or flexible skin contact substrate. This skin attachment layer 114 is sized to extend outwardly to the outermost perimeter of the housing 112 of the on-body injection device 104.

Figure 2:
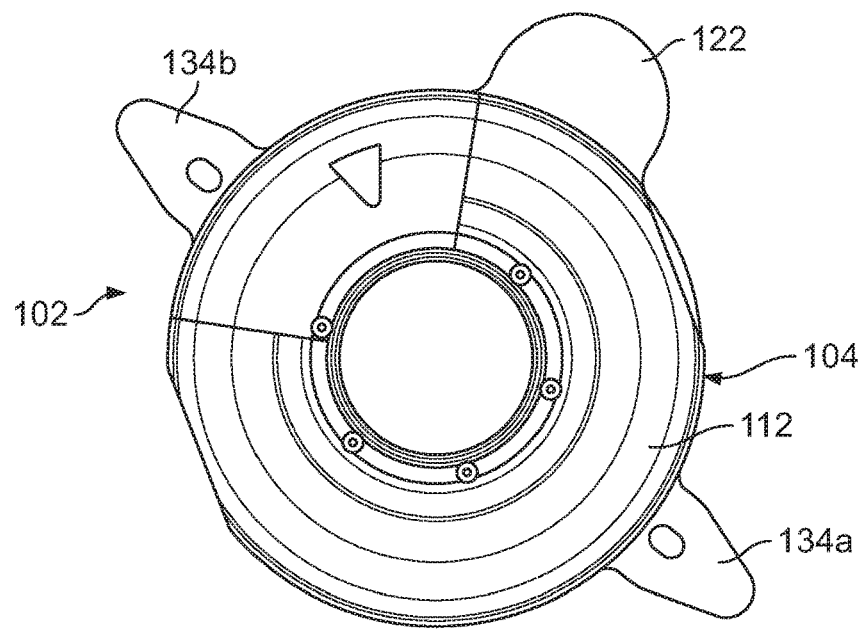
Figure 3:
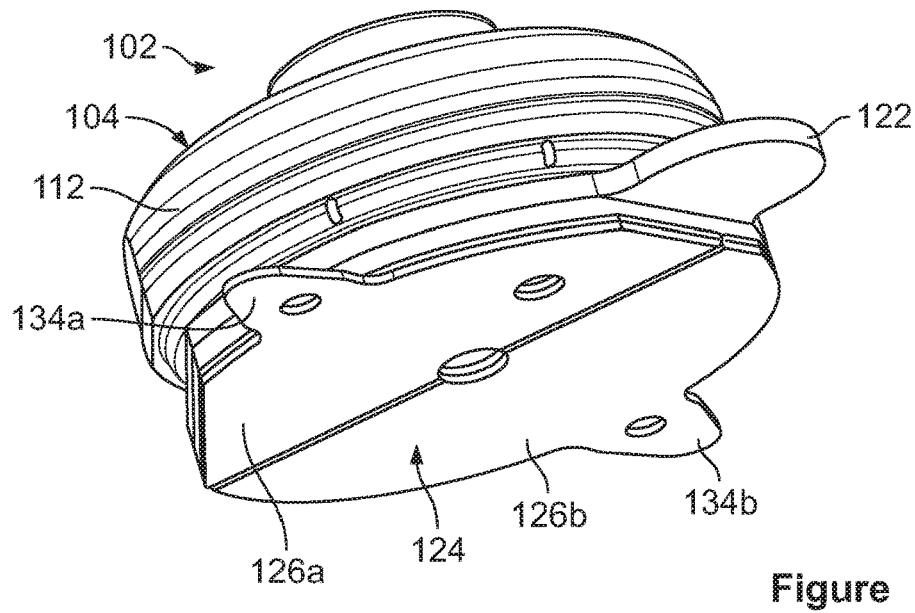
Figure 7:
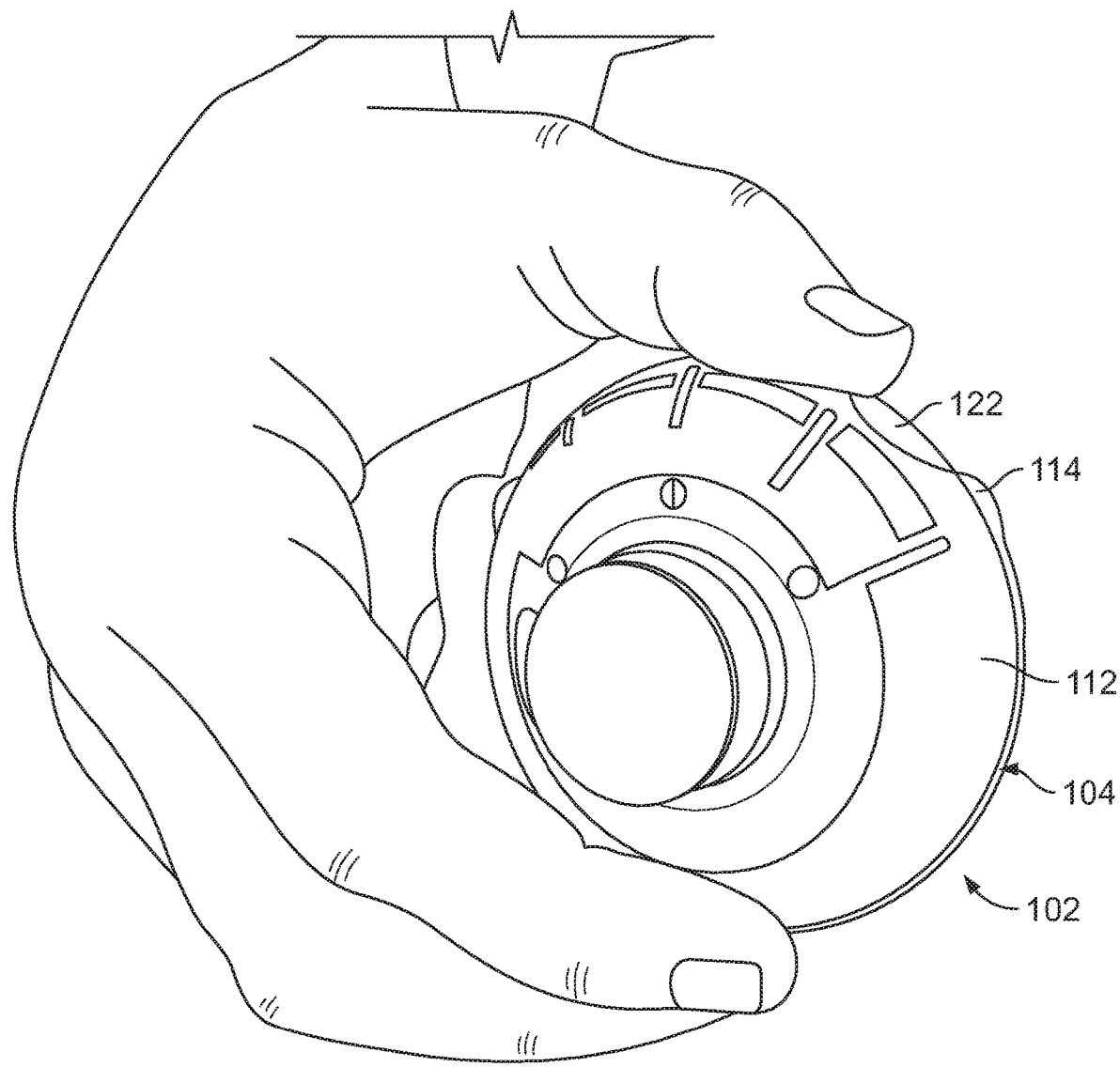
FIG. 7 illustrates removal of the injection device assembly of FIG. 1a from the skin of a patient after injection is completed.

The flexible skin contact substrate or skin attachment layer 114 also may include a radially extended portion forming a removal tab 122, which may be seen in FIGS. 1a, 2 and 3. Removal tab 122 enhances ease of removal from the patient. While the removal tab 122 is part of skin attachment layer 114, it is free of adhesive for ease of patient handling. When the patient wishes to remove the injection device 104 from an injection site on the patient's skin, the patient may grasp the injection device 104, with the removal tab 122 gripped against the edge of the injection device 104, and the injection device 104 may be lifted and twisted, thereby pulling the skin attachment layer 114 from the skin of the patient at an angle, as seen for example in FIG. 7.

The flexible skin contact substrate or skin attachment layer 114 on one side is preferably permanently bonded to the bottom surface 110 of the injection device housing 112 by a device side adhesive 116. The device side adhesive 116 may be any adhesive of suitable strength, for example a medical-grade acrylic adhesive. It may be seen in FIG. 1a that the device side adhesive 116 does not extend to the full peripheral edge of the injection device 104, and instead leaves a marginal or peripheral edge portion 118 of the flexible skin contact substrate or skin attachment layer 114 free of adhesive. As will be explained in more detail later, this provides for strain relief and enhanced conformation to the curves on a surface of a patient's body. Alternatively, the skin attachment layer 114 may be permanently bonded to the underside of the injection device by using suitable mechanical means, such as for example heat-staking or ultrasonic welding.

To adhere the injection device 104 to the skin of a patient during the injection, skin adhesive 120 is preferably provided along the entire surface of the opposed, skin-facing side of the skin attachment layer 114 (except for removal tab 122). The skin adhesive 120 may be made of any suitable adhesive of sufficient strength for the desired wear time and biocompatibility, for example, a medical-grade acrylic adhesive. With respect to strength, it should be noted that the skin adhesive 120 is, of course, weaker than the device side adhesive 116 to allow the injection device 104 and skin attachment layer 114 to be removed from the patient's skin after the injection is completed.

The skin adhesive 120 on the opposed side of the flexible skin contact substrate or skin attachment layer 114 is covered during shipping and storage with a release layer or liner 124 that must be removed to expose the skin adhesive 120 and allow attachment of the injection device 104 to the skin of a patient. In accordance with the present disclosure, the release layer 124 comprises a film constructed of a material, such as PET, that does not strongly adhere to the skin adhesive 120 and can be pulled away from the skin adhesive 120 with relatively low force for ease of manual removal.

More particularly, the release layer or liner 124 is formed of a plurality of folded film segments that are substantially contiguous, so as to cover the skin adhesive 120 and protect the skin adhesive 120 from inadvertent contact. As shown for illustration purposes, each folded segment includes a fold so as to be folded back along or over itself, and the fold extends along a fold line that substantially bisects the skin facing surface 110 of the housing 112, and divides the segment into a skin adhesive contact portion that is releasably adhered to the skin adhesive 120 and a free portion that is connected to and below the skin adhesive contact portion and that is operable upon tensioning to progressively pull the skin adhesive contact portion away from the skin adhesive 120 along a peel line that offers lower resistance to removal as compared to simultaneous removal of the release layer 124 over the entire surface area of the skin adhesive 120.

In the illustrated embodiment, as may be seen in FIGS. 1a-4c, there are two folded film segments 126a and 126b, each of which is generally circular and folded back along or over itself at a fold line along the diameter, so as to have each segment form a semicircular or half-circle shape when folded.

As generally described above, each film segment 126a, 126b has a respective fold line 128a, 128b, dividing each segment into a skin adhesive contact portion 130a, 130b that is releasably adhered to the skin adhesive 120, and a free portion 132a, 132b that is folded back along itself and under the skin adhesive contact portion 130a, 130b. Thus, each of the folded film segments 126a, 126b covers substantially half of the collective skin adhesive contact portion 130a, 130b. More than two segments could be used, if desired, such as for example by using a plurality of segments having a pie-shape or other configuration. The free portion 132a, 132b can be tensioned downwardly to pull the respective skin adhesive contact portion 130a, 130b away from the skin adhesive 120 along a peel line that gradually moves or progresses from the fold line 128a, 128b to the marginal edge of the skin adhesive contact portion 130a, 130b as downward tension continues to be applied to the free portion 132a, 132b and the skin adhesive contact portion 130a, 130b is gradually and progressively pulled away from the skin adhesive 120.

Figure 4A:
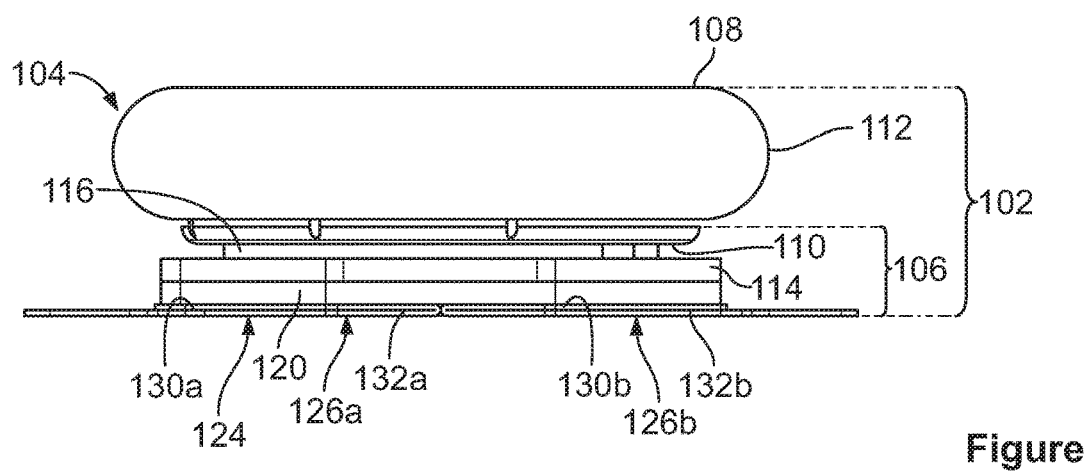
FIGS. 4a-4c diagrammatically illustrate the on-body injection device assembly gradually being pulled away from a support surface, such as the support surface of a transfer device (or other packaging) with a skin adhesive release liner being simultaneously pulled away from the skin adhesive on the underside of the injection device.
Figure 4B:
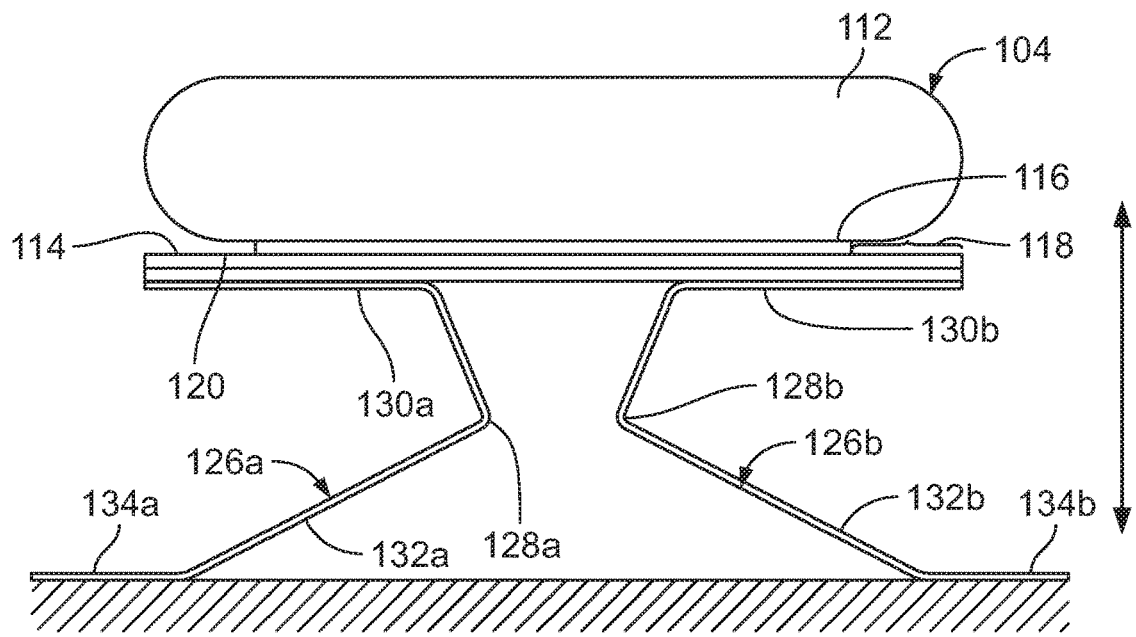
Figure 4C:
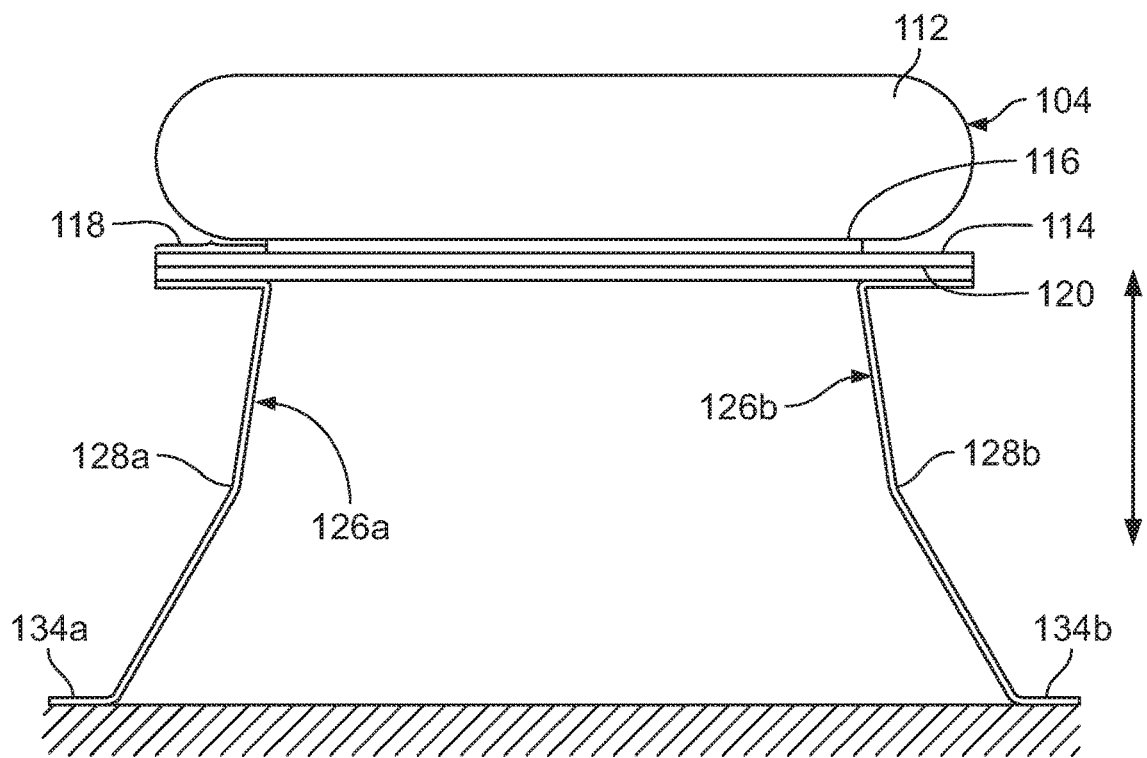
Figure 5A:
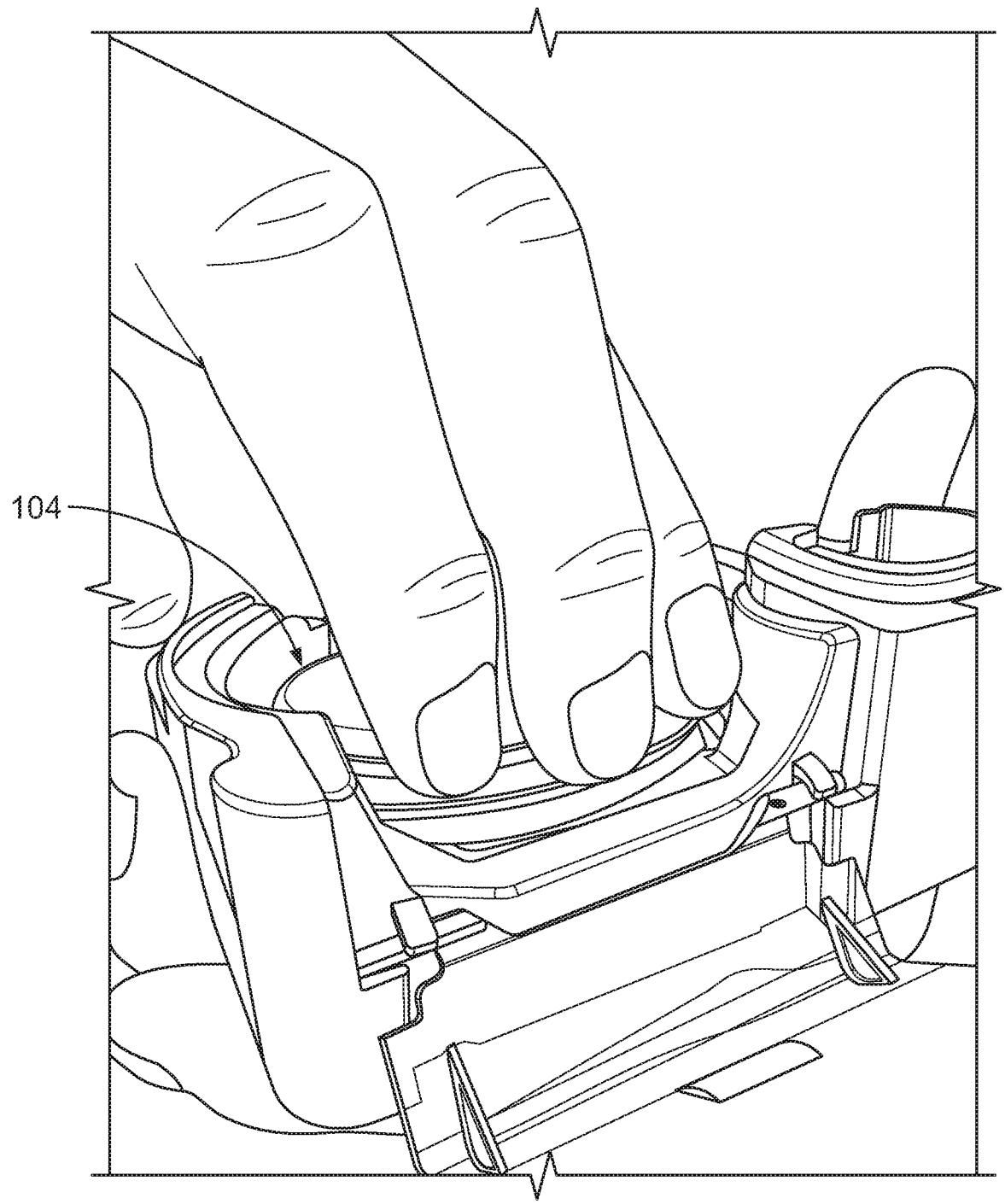
FIGS. 5a-5e illustrate an on-body injection device assembly being gradually pulled away from a support surface with a skin adhesive release liner being simultaneously pulled away from the skin adhesive on the underside of the injection device.
Figure 5B:
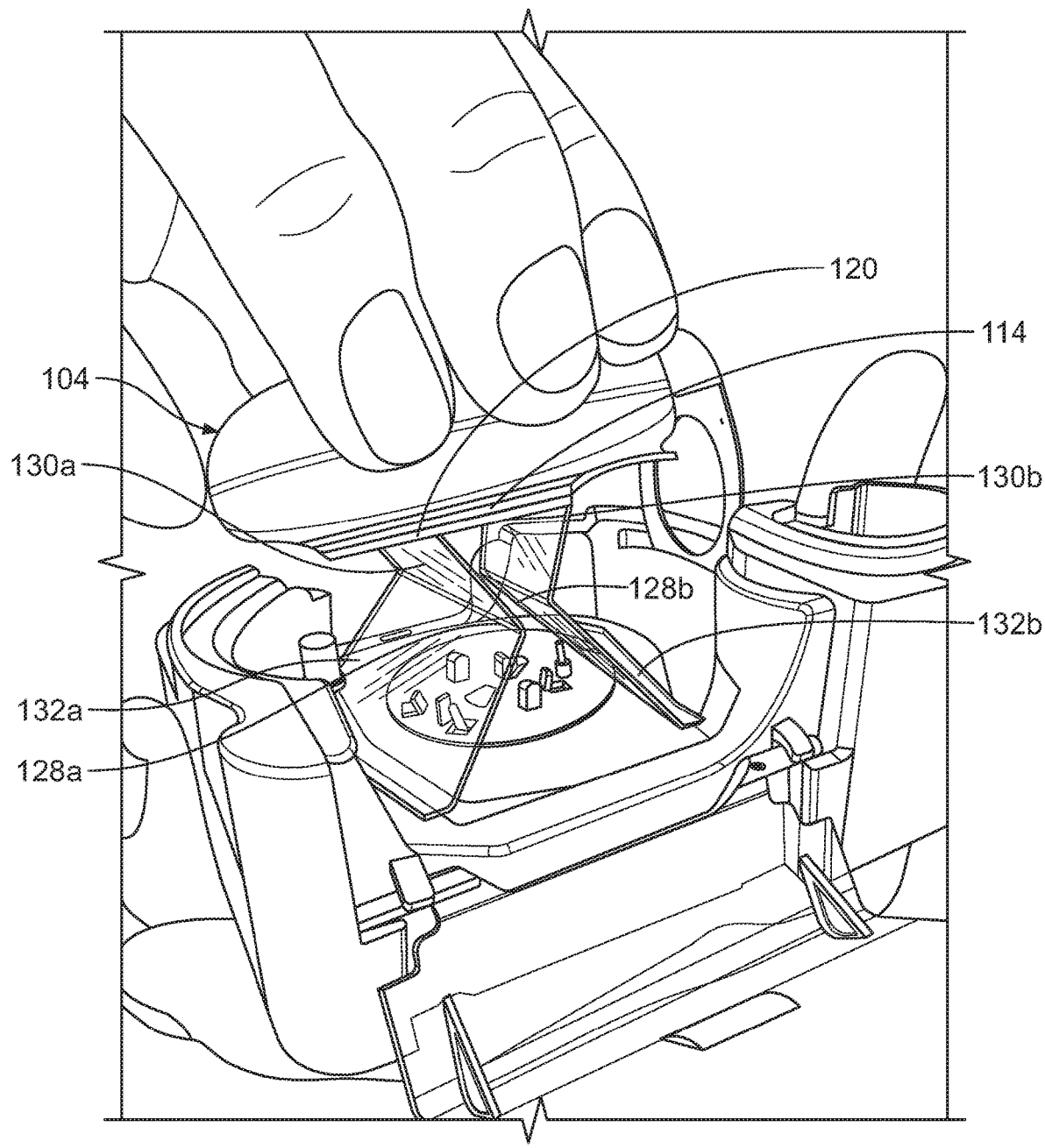
Figure 5C:
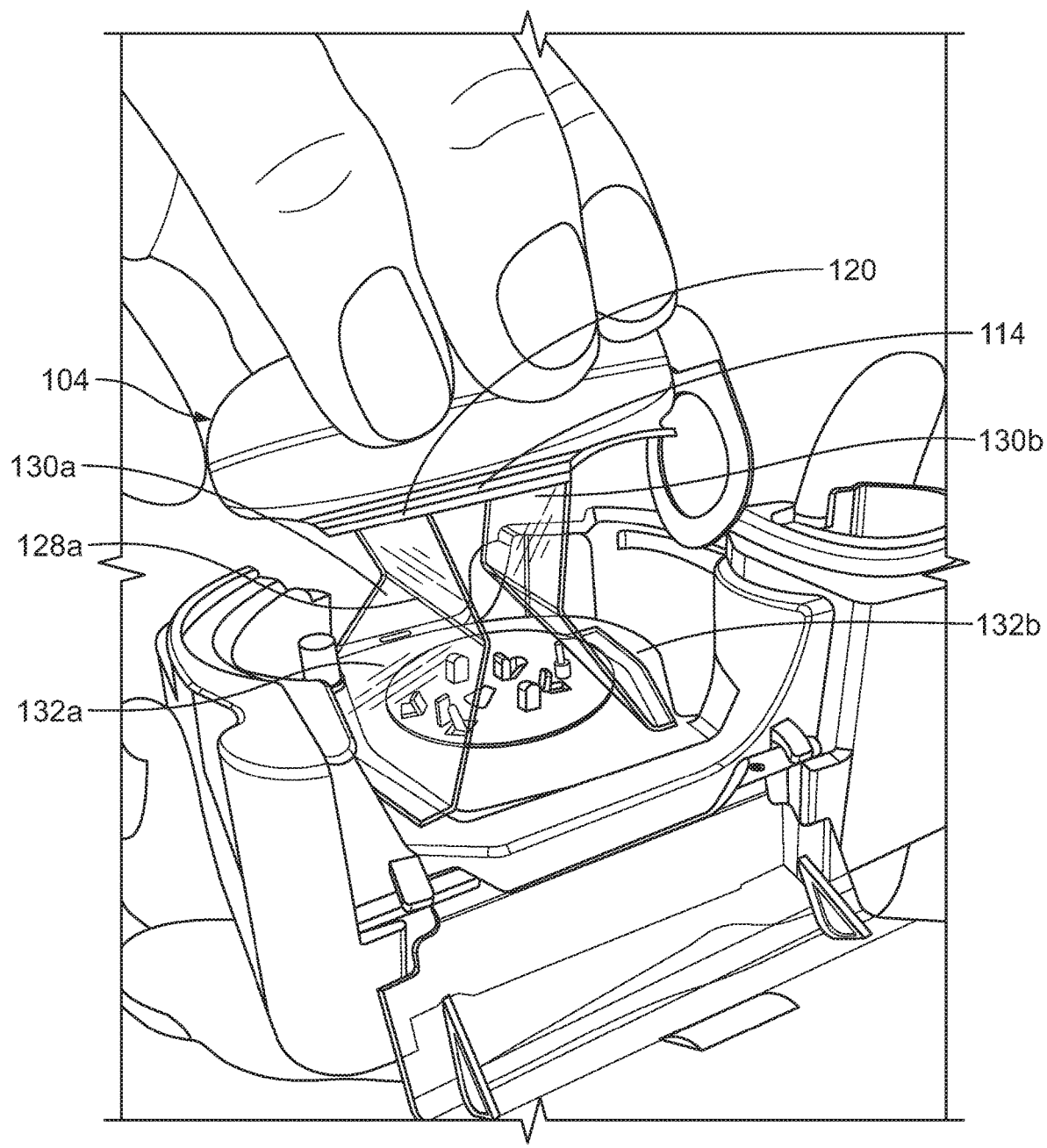
Figure 5D:
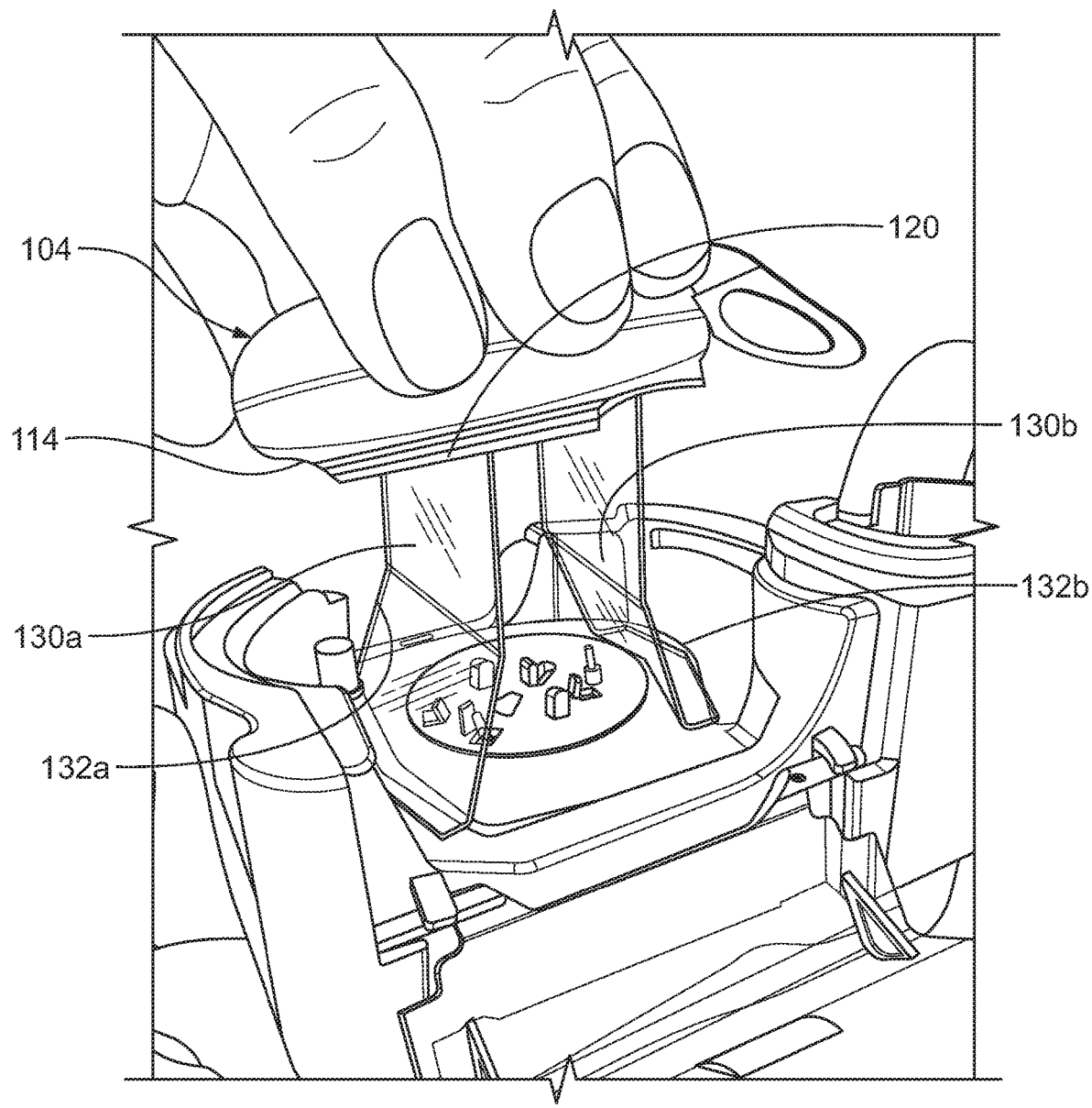
Figure 5E:
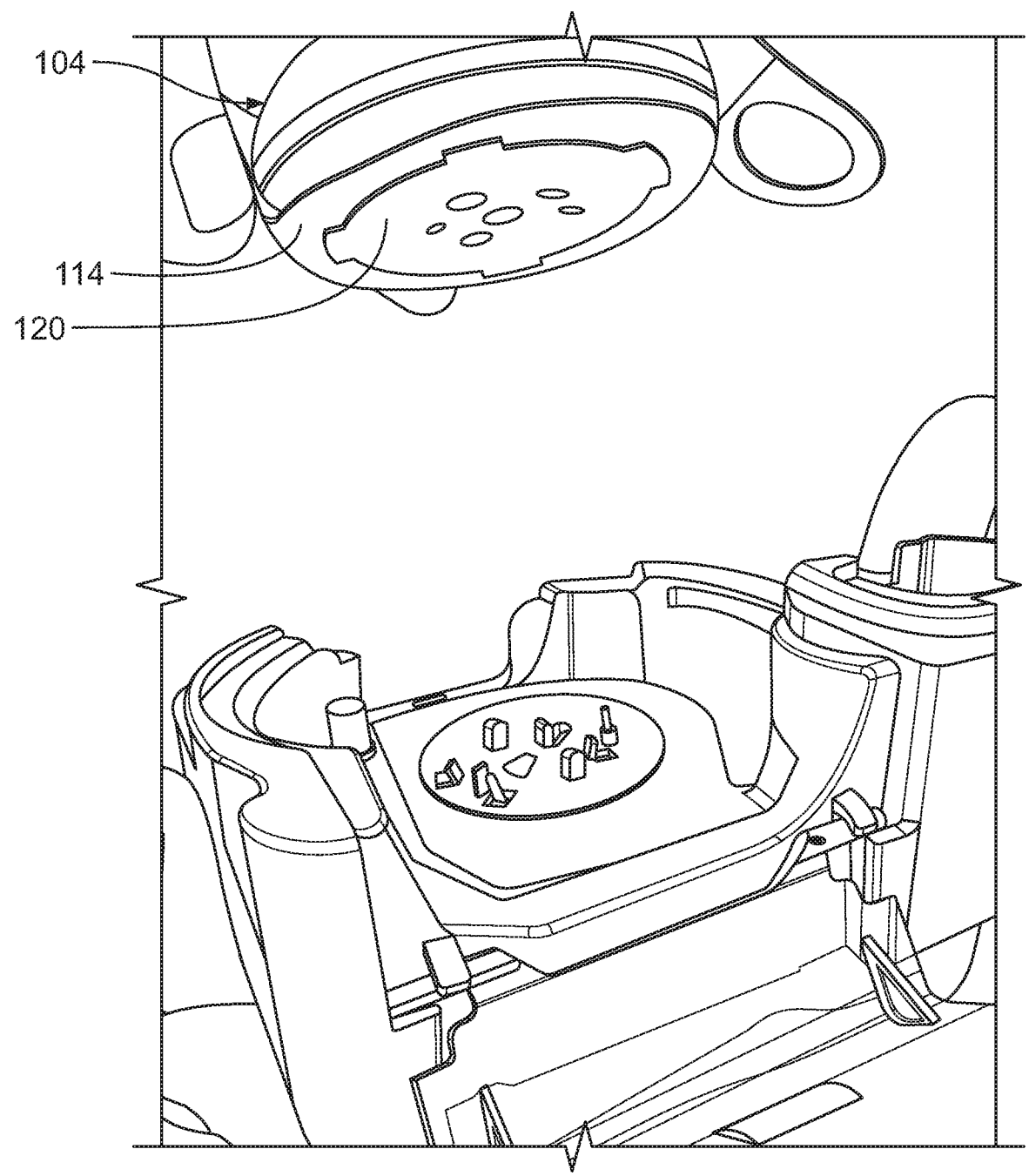
Figure 6A:
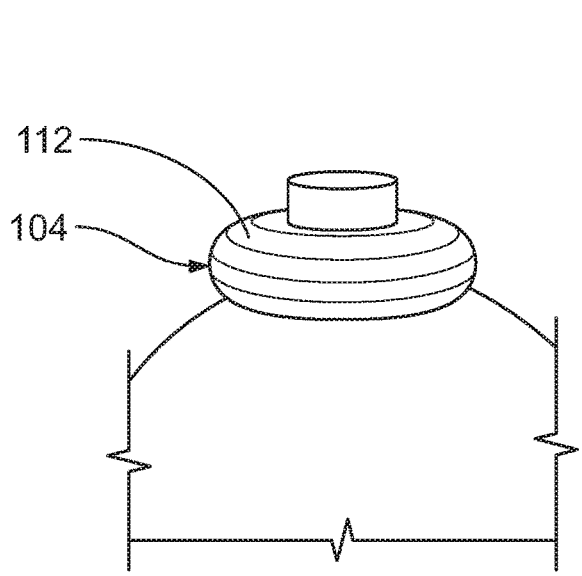
FIGS. 6a-6d illustrate, using a balloon, benefits of the skin adhesive structure incorporated in the injection device assembly of FIG. 1a in conforming to differing body shapes.
Figure 6B:
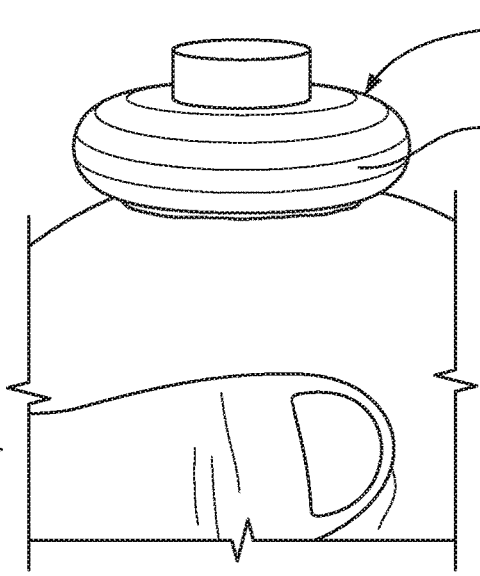
Figure 6C:
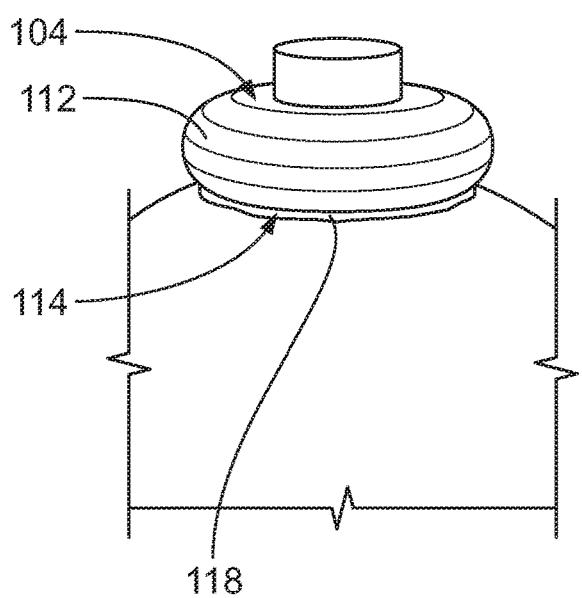
Figure 6D:
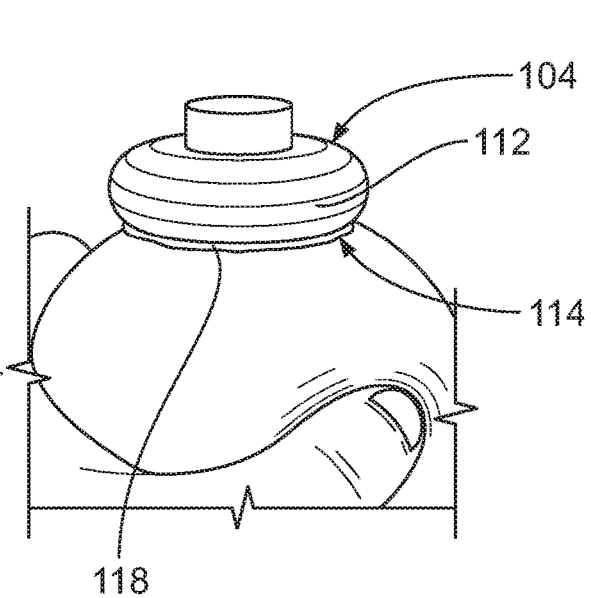

The removal of the release layer 124 is shown diagrammatically in FIGS. 4a-4c and relative to an on-body injection device 104 in FIGS. 5a-5e. As shown in successive steps and described above, an injection device 104 with an adhesive structure 106 is gradually separated from a support surface, which could be a support surface of any suitable fluid transfer device or packaging, or other suitable structure. As the injection device 104 is separated from the support surface, the free portions 132a, 132b of the film segments 126a, 126b (which are secured to the support surface at radially extending mounting tabs 134a, 134b that are located 180 degrees apart) begin to pull or peel the skin adhesive contact portions 130a, 130b away from the skin adhesive 120 located on the underside of flexible skin contact substrate or skin attachment layer 114.

The pulling or peeling away of the release liner film segments 126a, 126b starts at the fold lines 128a, 128b, and the peel line 136a, 136b between the release layer 124 and skin adhesive 120 gradually progresses outwardly along each segment 126a, 126b as the distance between the injection device 104 and support surface increases, until the film segments 126a, 126b are fully removed from the underside of the skin attachment layer 114. This allows the user to immediately place the injection device 104 on the patient's skin without delay or having to fumble with separately removing the release layer 124. The bi-folded segments 126a, 126b allow for a very smooth, easy removal of the release layer 124. Also, the fold lines 128a, 128b, where the segments 126a, 126b are folded back onto themselves, provide for the initiation of peel points or lines between the release layer 124 and skin adhesive 120 for separation of the film of the release layer 124 from the skin adhesive 120.

As noted earlier, there is no device side adhesive 116 along the marginal edge portion 118 of the flexible skin contact substrate or skin attachment layer 114 (see FIGS. 1b, 4a and 4b). This permits the skin attachment layer 114 to better conform to the shape of the patient's body or curves or undulations of a patient's skin at the location of attachment to the patient. FIGS. 6a-6d help illustrate this, by employing a balloon to model a curved skin surface. The marginal edge portion 118 of the skin attachment layer 114 can flex with the skin providing a strain relief that helps avoid inadvertent or premature separation of the injection device from the patient.

Figure 8B:
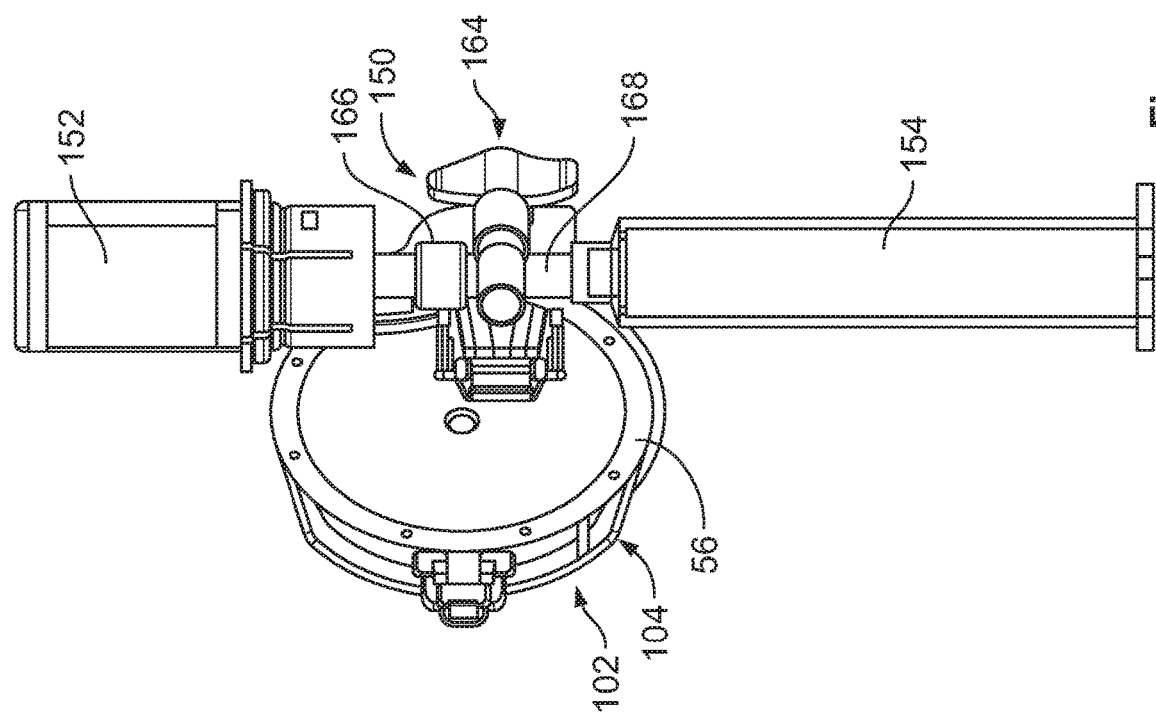
FIG. 8b is a perspective view of the combination of FIG. 8a, taken from a different viewing angle.
Figure 8A:
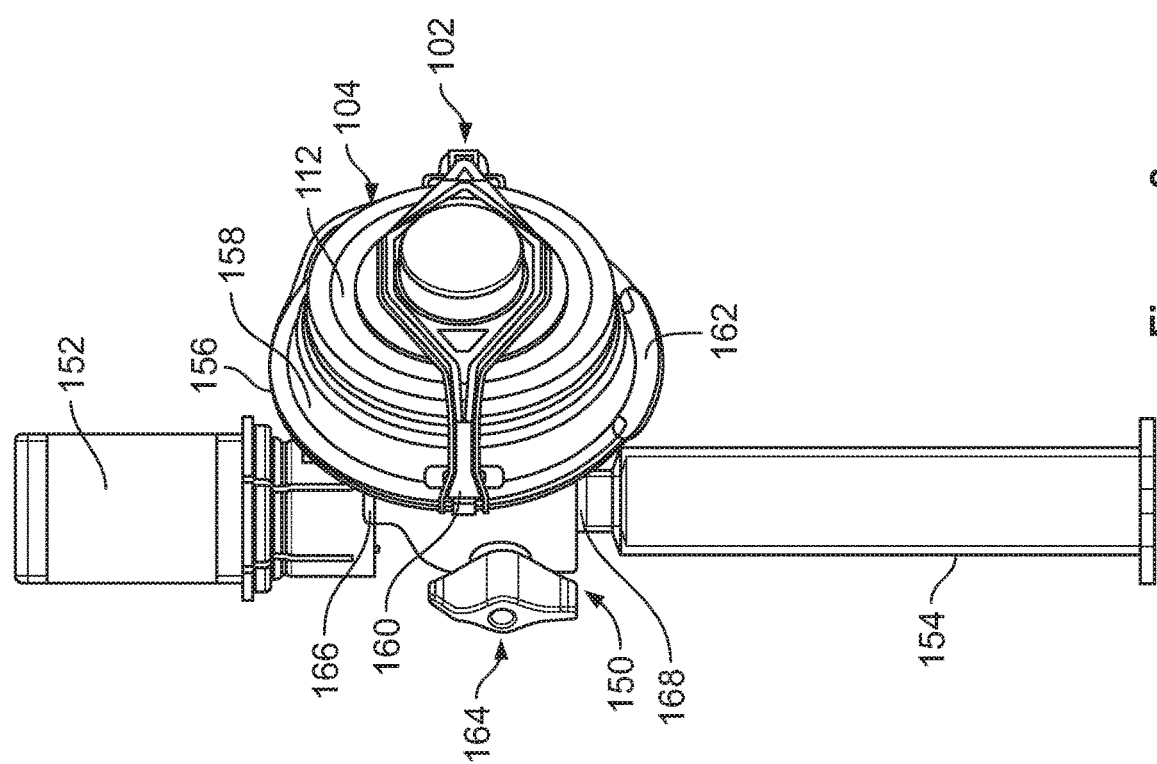
FIG. 8a is a perspective view, taken from one viewing angle, of a combination of the on-body medical fluid injection device with adhesive assembly of FIG. 1a and a medical fluid transfer device, with a standard medical drug vial and syringe attached thereto.

Turning to FIGS. 8a and 8b, these figures depict, for purposes of illustration and not limitation, an assembled transfer system comprising the injection device assembly 102 mounted on a support surface of a medical fluid transfer device 150, with vial 152 and syringe 154 attached to the transfer device 150. This particular transfer device (also shown in the simultaneously filed U.S. provisional patent application No. 62/571,419, filed on the same day herewith and incorporated by reference above) is shown for purposes of illustration only and not limitation. Other transfer devices of other configurations may be used without departing from the claimed subject matter.

FIGS. 8a and 8b are taken from different viewing angles, allowing the assembly to be viewed from opposite sides of the transfer device 150. As labeled in the figures, the illustrated transfer device 104 includes a transfer device base 156, one side of which forms a support surface 158, against which the injection device 104 rests, as seen in FIG. 8a. A harness or retainer 160 holds the injection device 104 on the transfer device base 156 within a peripheral ring or ring structure 162 that is attached to the base 156. Optional valve assembly or subassembly 164, such as a three-way stopcock valve assembly, is mounted on the underside of the transfer device base 156 and provides selective fluid communication among the medical fluid vial 152, syringe 154 and injection device 104 when they are, respectively, secured to the valve subassembly vial port 166, syringe port 168 and upstanding injection device fluid transfer port 170 associated with the valve subassembly 164, The basic operating principles for fluid transfer in this embodiment are essentially the same as previously described in the above identified application (U.S. provisional patent application No. 62/571,419) incorporated by reference herein.

Figure 9:
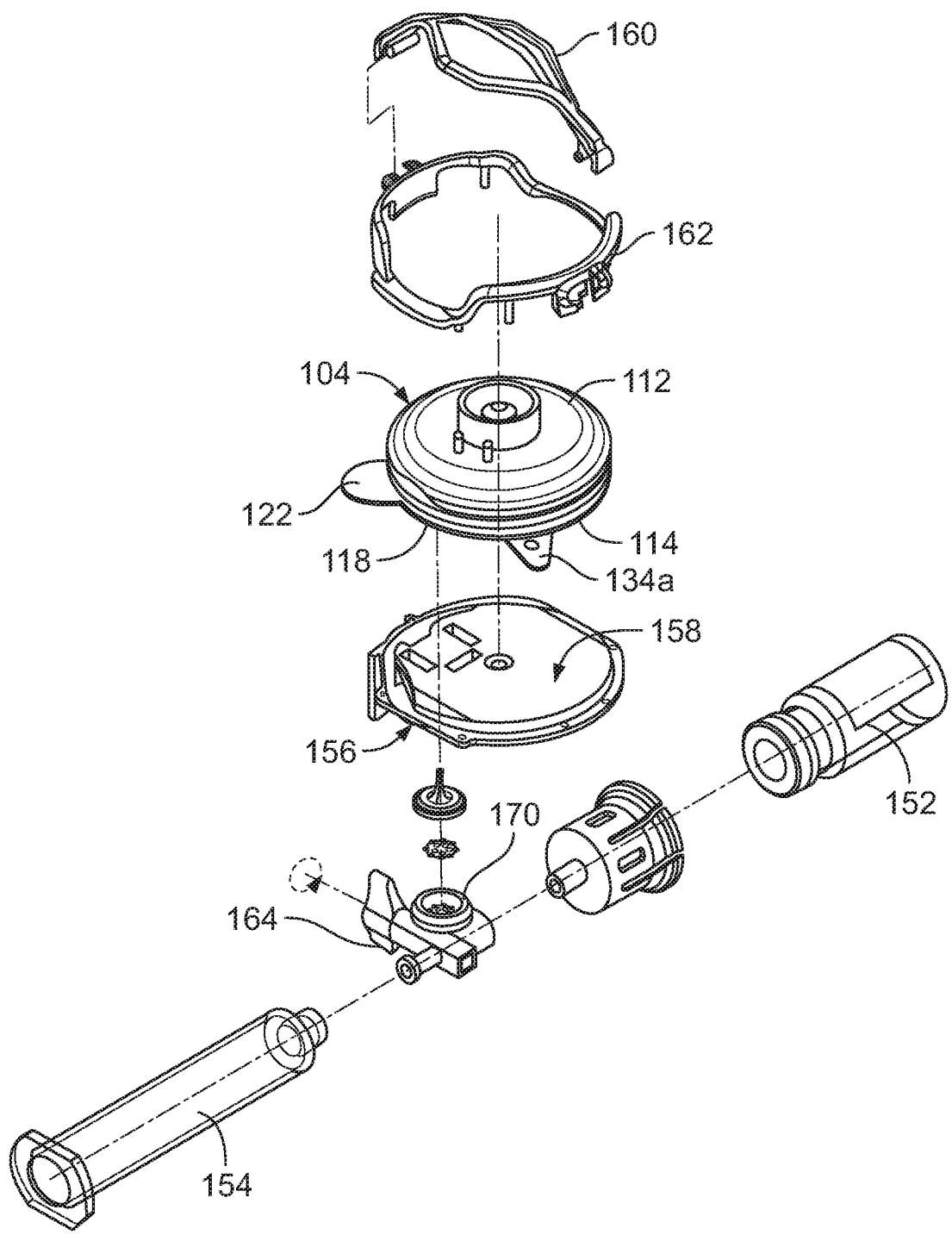

Referring to FIG. 9, one side of the transfer device base 156 in this embodiment (which may be referred to as the top side or upper side for convenience only) provides the planar support surface 158 upon which the injection device 104 rests when secured to the base 156 by retainer 160, The radially projecting mounting tabs 134a, 134b, best seen in FIGS. 2 and 3, are attached to the transfer device, for example to the ring structure or other connection area, so that the free portions 132a, 132b of the folded segments 126a, 126b of the release layer 124 pull on the skin adhesive contact portions 130a, 130b of the folded segments 126a, 126b as the injection device 104 is lifted from the support surface 158 of the transfer device 150—operating in the same manner to remove the release layer as shown in FIGS. 4a-4c and 5a-5e. Thus, the free portion 132a, 132b of each folded film segment 126a, 126b includes a release connection to an extended mounting tab 134a, 134b of the release layer 124 and the transfer device 150 is configured to engage the release connection 124. In this example, the release connection is present at an extension 134a, 134b of the folded film segment 126a, 126b and the transfer device 150 includes an engaging surface configured to connect to the extension of the folded film segment 126a, 126b.

Although the present subject matter is described herein with reference to specific structures, methods and examples, this is for purposes of illustration only, and it is understood that the present subject matter is applicable to a large range of devices and systems that may differ in particular configuration and appearance while still employing this subject matter. See the claims set forth below for the scope of the present subject matter. This patent is only limited by the appended claims and legal equivalents thereof.

The invention claimed is:

1. An on-body medical fluid injection device with adhesive assembly comprising:
    a housing configured to receive a supply of medical fluid;
    an injection needle carried by the housing and movable between a retracted position within the housing and an injection position extending from the housing;
    the housing further including a skin facing surface that faces the skin of a patient when the on-body injection device is on the patient's body;
    skin adhesive carried by at least a portion of the skin-facing surface for securing the housing to the patient's skin during an injection; and
    a pair of substantially contiguous folded film segments covering the skin adhesive, each film segment including a fold line dividing the film segment into an adhesive contact portion that covers substantially half of the skin adhesive and is releasably adhered to the skin adhesive, and a free portion that is operable upon tensioning to progressively pull the adhesive contact portion away from the skin adhesive, wherein each of the folded film segments includes a fold that extends along the fold line that substantially bisects the skin facing surface of the housing.

2. The on-body medical fluid injection device with adhesive assembly of claim 1 further comprising a flexible skin contact substrate that is attached on one side to the skin facing surface of the housing of the on-body injection device and on an opposed side carries the skin adhesive.

3. The on-body medical fluid injection device with adhesive assembly of claim 2 wherein a peripheral edge portion of We flexible skin contact substrate is not attached to the skin facing surface of the on-body injection device on the one side and on the opposed side carries the skin adhesive for adhering to the skin of the patient, whereby the peripheral edge portion that is not attached to the skin facing surface of the on-body injection device allows the flexible skin contact substrate to better conform to the patient.

4. A medical device comprising a medical fluid injection device and a fluid transfer device configured for holding medical fluid in cooperative relation therewith:
    the medical fluid injection device comprising:
        a housing configured to receive a supply of medical fluid;
        an injection needle carried by the housing and movable between a retracted position within the housing and an injection position extending from the housing;
        the housing further including a skin facing surface that faces the skin of a patient when the medical fluid injection device is on the patient's skin;
        skin adhesive carried by at least a portion of the skin facing surface of the housing for securing the housing to the patient's skin during injection;
        a plurality of substantially contiguous folded film segments covering the skin adhesive, each folded film segment including a fold line dividing the film segment into an adhesive contact portion that is releasably adhered to the skin adhesive, and a free portion that is operable upon tensioning to progressively pull the adhesive contact portion away from the skin adhesive;
    the fluid transfer device comprising:
        a base having a support surface, and being configured to releasably retain the medical fluid injection device on the support surface of the base; and
        the transfer device further being configured to engage each free portion of each film segment, whereby upon release of the medical fluid injection device from the base and separation of the medical fluid injection device from the support surface of the base, the transfer device exerts a tensioning force on the free portion of each folded film segment to remove the plurality of film segments from the skin adhesive.

5. The medical device of claim 4 wherein the free portion of each folded film segment includes a release connection to an extended mounting tab of a release layer and the transfer device is configured to engage the release connection.

6. The medical device of claim 5 in which the release connection of each folded film segment comprises an extension of the folded film segment and the transfer device includes an engaging surface configured to connect to the extension of the folded film segment.

\* \* \* \* \*